(12) United States Patent
Enders et al.

(10) Patent No.: US 12,327,635 B2
(45) Date of Patent: Jun. 10, 2025

(54) COMPUTER-IMPLEMENTED METHOD AND SYSTEM FOR TRAINING AN EVALUATION ALGORITHM, COMPUTER PROGRAM AND ELECTRONICALLY READABLE DATA CARRIER

(71) Applicant: Siemens Healthcare GmbH, Erlangen (DE)

(72) Inventors: Frank Enders, Erlangen (DE); Dorothea Roth, Nuremberg (DE); Michael Schrapp, Munich (DE); Matthias Senn, Uttenreuth (DE); Michael Suehling, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 330 days.

(21) Appl. No.: 17/308,134

(22) Filed: May 5, 2021

(65) Prior Publication Data

US 2021/0357689 A1    Nov. 18, 2021

(30) Foreign Application Priority Data

May 13, 2020    (DE) .................... 10 2020 206 059.2

(51) Int. Cl.
*G16H 50/20*    (2018.01)
*G06F 18/214*   (2023.01)
(Continued)

(52) U.S. Cl.
CPC ........... *G16H 50/20* (2018.01); *G06F 18/214* (2023.01); *G06N 20/00* (2019.01); *G06T 7/0012* (2013.01);
(Continued)

(58) Field of Classification Search
CPC ........ G16H 50/20; G16H 30/20; G16H 30/40; G06F 18/214; G06N 20/00; G06T 7/0012; G06T 2207/20081
See application file for complete search history.

(56) References Cited

U.S. PATENT DOCUMENTS

2018/0129900 A1*  5/2018  Kiraly ................... G06N 3/045
2019/0130565 A1*  5/2019  Lee .......................... G06N 3/08
(Continued)

FOREIGN PATENT DOCUMENTS

CN    110033859 A    7/2019
EP      3511941 A1    7/2019

*Primary Examiner* — Nay A Maung
*Assistant Examiner* — Dustin Bilodeau
(74) *Attorney, Agent, or Firm* — Harness, Dickey & Pierce, P.L.C.

(57) ABSTRACT

A computer-implemented method for the further training of an artificial-intelligence evaluation algorithm that has already been trained based upon basic training data, wherein the evaluation algorithm ascertains output data describing evaluation results from input data comprising image data recorded with a respective medical imaging facility. In an embodiment, the method includes ascertaining at least one additional training data set containing training input data and training output data assigned thereto; and training the evaluation algorithm using the at least one additional training data set. The additional training data set is ascertained from the input data used during a clinical examination process with a medical imaging facility, which the already-trained evaluation algorithm was used, and output data of the already-trained evaluation algorithm that has been at least partially correctively modified by the user.

23 Claims, 5 Drawing Sheets

(51) Int. Cl.
  *G06N 20/00* (2019.01)
  *G06T 7/00* (2017.01)
  *G06V 10/764* (2022.01)
  *G06V 10/774* (2022.01)
  *G16H 30/20* (2018.01)
  *G16H 30/40* (2018.01)

(52) U.S. Cl.
  CPC .......... *G06V 10/764* (2022.01); *G06V 10/774* (2022.01); *G16H 30/20* (2018.01); *G16H 30/40* (2018.01); *G06T 2207/20081* (2013.01)

(56) References Cited

U.S. PATENT DOCUMENTS

| | | | |
|---|---|---|---|
| 2019/0221304 A1 | 7/2019 | Ionasec | |
| 2020/0042903 A1* | 2/2020 | Moazzami | G06N 20/20 |
| 2020/0167677 A1* | 5/2020 | Verma | G06N 3/042 |
| 2020/0242470 A1* | 7/2020 | Menkovski | G06N 3/08 |
| 2021/0201208 A1* | 7/2021 | Bhole | G06F 18/214 |

* cited by examiner

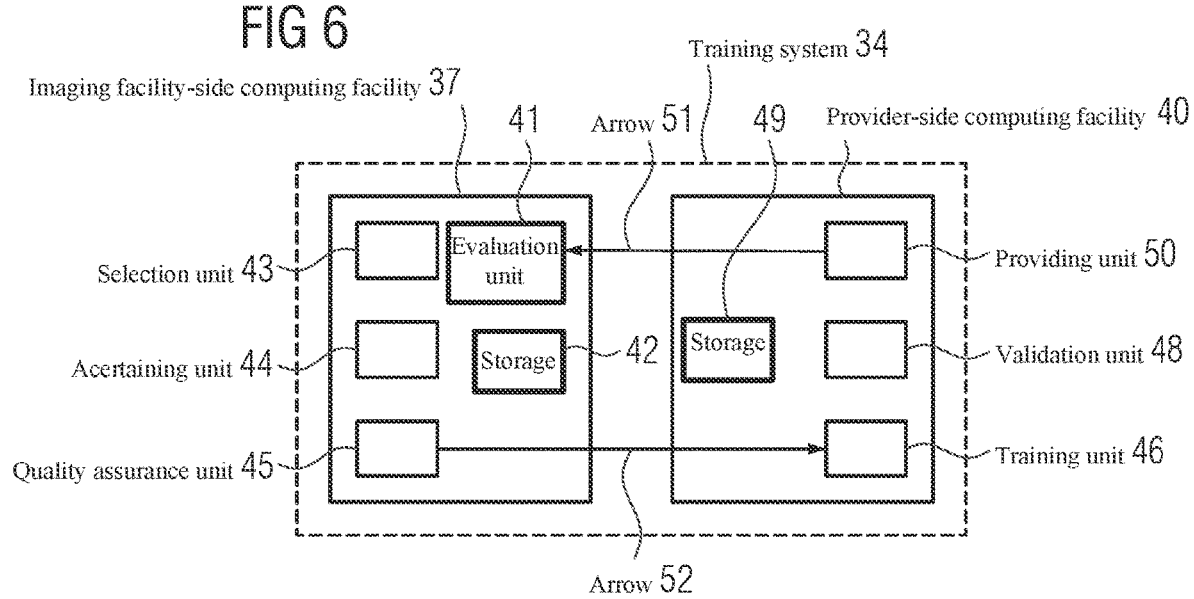

COMPUTER-IMPLEMENTED METHOD AND SYSTEM FOR TRAINING AN EVALUATION ALGORITHM, COMPUTER PROGRAM AND ELECTRONICALLY READABLE DATA CARRIER

PRIORITY STATEMENT

The present application hereby claims priority under 35 U.S.C. § 119 to German patent application number DE 102020206059.2 filed May 13, 2020, the entire contents of which are hereby incorporated herein by reference.

FIELD

Example embodiments of the invention generally relate to a computer-implemented method and a training system for the further training of an artificial intelligence algorithm that has already been trained based upon basic training data, wherein the evaluation algorithm ascertains output data describing evaluation results from input data comprising image data recorded with a respective medical imaging facility; and/or to a computer program and an electronically readable data carrier.

BACKGROUND

Medical imaging is becoming increasingly important in both diagnostics and therapy. For example, methods such as computed tomography, magnetic resonance imaging or sonography can be used to obtain volume image data and sectional image data of the interior of a body of an examination object and display them on an appropriate medium. The image data obtained from imaging is now generally available in digital form and can be stored, analyzed and processed by means of data technology. This produces large amounts of image data, parts of which are difficult to interpret. Furthermore, there is a large number of applications in which image data is created in preliminary recordings that are to be used for planning further examinations and/or therapeutic measures. This gives rise to the frequently complex task of deriving suitable control data for the imaging facility or a further medical-technical facility from the image data.

To address these complex tasks, the use of artificial-intelligence algorithms trained by machine learning has been suggested in the prior art. Such artificial-intelligence algorithms are frequently referred to as trained functions. Image data from medical imaging facilities can be evaluated by artificial-intelligence evaluation algorithms in order to obtain output data that can be used as the basis for a control task, a diagnosis to be made by a physician and/or another type of decision. The development and use of such evaluation algorithms are increasing rapidly for clinical applications.

Such evaluation algorithms that are intended to be used on computing facilities that are part of an imaging facility or assigned thereto are usually delivered as a finished product and remain unchanged in use. If, however, they are updated by further training, according to the prior art, this only takes place after very long periods of time, for example after several months or years, when the next software version is released. Herein, training data, whether for the original training of the evaluation algorithm or for further training, i.e. updating, of the evaluation algorithm is collected manually from clinical facilities, in particular those that are in collaboration with the provider of the evaluation algorithm, which is frequently also the manufacturer of the imaging facility. This process is extremely slow and its implementation is in particular highly questionable in view of the high number of artificial-intelligence evaluation algorithms. Herein, on the other hand, it would be extremely advantageous to update evaluation algorithms since this would increase their robustness and reliability and enable more efficient scanning or data processing.

A further disadvantage of the fact that training data is usually compiled manually, in particular in predefined manageable user groups, is that important and useful additional training data that arises in daily clinical practice can be lost and therefore cannot be used to improve the artificial-intelligence evaluation algorithm.

SUMMARY

At least one embodiment of the invention is based on disclosing a possibility for the improvement of artificial-intelligence evaluation algorithms to evaluate image data that are easy to implement and/or can be performed on a frequent basis.

At least one embodiment of the invention is directed to a method, training system, computer program and/or electronically readable data carrier. Advantageous embodiments are derived from the claims.

The following describes embodiments of the invention in relation to the method, the training system and the computer program. Features, advantages or alternative embodiments mentioned herein can similarly also be transferred to the other subject matter and vice versa. In other words, the substantive claims (which are, for example, directed at the training system) can also be developed with the features described or claimed in connection with a method and vice versa. Herein, the corresponding functional features of the method are embodied by corresponding substantive modules or subunits of the computer program.

With a computer-implemented method of an embodiment, it is provided that the additional training data set is ascertained from the input data used during a clinical examination process with a medical imaging facility, in which the already-trained evaluation algorithm was used, and output data of the already-trained evaluation algorithm that has been at least partially correctively modified by the user.

At least one embodiment of the present invention relates to a computer-implemented method for further training of an artificial-intelligence evaluation algorithm that has already been trained based upon basic training data, the artificial-intelligence evaluation algorithm ascertaining output data describing evaluation results from input data including image data recorded with a medical imaging facility, the computer-implemented method comprising:

ascertaining at least one additional training data set containing training input data and correspondingly assigned training output data; and training the artificial-intelligence evaluation algorithm using the at least one additional training data set ascertained, wherein the at least one additional training data set is ascertained from the input data used during a clinical examination process with the medical imaging facility, in which the already-trained evaluation algorithm was used, and output data of the already-trained evaluation algorithm that has been at least partially correctively modified by the user.

In addition to the method, at least one embodiment of the present invention also relates to a training system having at least one medical imaging facility with a computing facility assigned to the imaging facility, which is embodied to execute an artificial-intelligence evaluation algorithm that has already been trained based upon basic training data, which ascertains output data describing evaluation results from input data comprising image data recorded with the medical imaging facility, and a computing facility provided by the provider of the evaluation algorithm, which is connected to the at least one imaging facility-side computing facility via a communication link, wherein the computing facilities comprise:

an ascertaining unit for ascertaining at least one additional training data set containing training input data and training output data assigned thereto, and a training unit for training the evaluation algorithm using the at least one additional training data set, wherein the ascertaining unit is embodied to ascertain the additional training data set from the input data used during a clinical examination process with a medical imaging facility, in which the already-trained evaluation algorithm was used, and output data of the already-trained evaluation algorithm that has been at least partially correctively modified by the user.

A computer program according to at least one embodiment of the invention can, for example, be loaded directly into storage means of the computing facilities of a training system according to at least one embodiment of the invention and has program segments for executing the steps of a method according to at least one embodiment of the invention when the computer program is executed in the computing facilities of the training system. The computer program can be stored on an electronically readable data carrier according to at least one embodiment of the invention, which therefore comprises electronically readable control information stored thereon, which comprises at least one computer program according to at least one embodiment of the invention and is embodied such that, when the data carrier is used in a training system according to at least one embodiment of the invention, it performs a method according to at least one embodiment of the invention.

A storage device can be implemented as a non-permanent main memory (random access memory, RAM for short) or as a permanent mass storage facility (hard disk, USB stick, SD card, solid state disk).

A training system according to at least one embodiment of the invention, comprises:

at least one medical imaging facility including a computing facility assigned to the at least one imaging facility, embodied to execute an artificial-intelligence evaluation algorithm that has already been trained based upon basic training data, which ascertains output data describing evaluation results from input data including image data recorded with the medical imaging facility; and a computing facility provided by a provider of the evaluation algorithm, the computing facility being connected to the at least one imaging facility-side computing facility via a communication link, at least one of the computing facility and the at least one imaging facility-side computing facility comprising:

an ascertaining unit for ascertaining at least one additional training data set containing training input data and correspondingly assigned training output data, and a training unit for training the artificial-intelligence evaluation algorithm using the at least one additional training data set, wherein the ascertaining unit is embodied to ascertain the additional training data set from the input data used during a clinical examination process with a medical imaging facility, in which the already-trained evaluation algorithm was used, and output data of the already-trained evaluation algorithm that has been at least partially correctively modified by the user.

A non-transitory computer program product, including a computer program, to enable a training system to perform the method of an embodiment, when the computer program is executed on the training system.

An electronically readable data carrier storing a computer program to enable a training system to perform the method of an embodiment, when the computer program is executed on the training system.

BRIEF DESCRIPTION OF THE DRAWINGS

Further advantages and details of the present invention may be derived from the example embodiments described below and with reference to the drawing, in which:

FIG. 6 shows the functional structure of the computing facilities of the training system in a second example embodiment.

DETAILED DESCRIPTION OF THE EXAMPLE EMBODIMENTS

Figure 1:
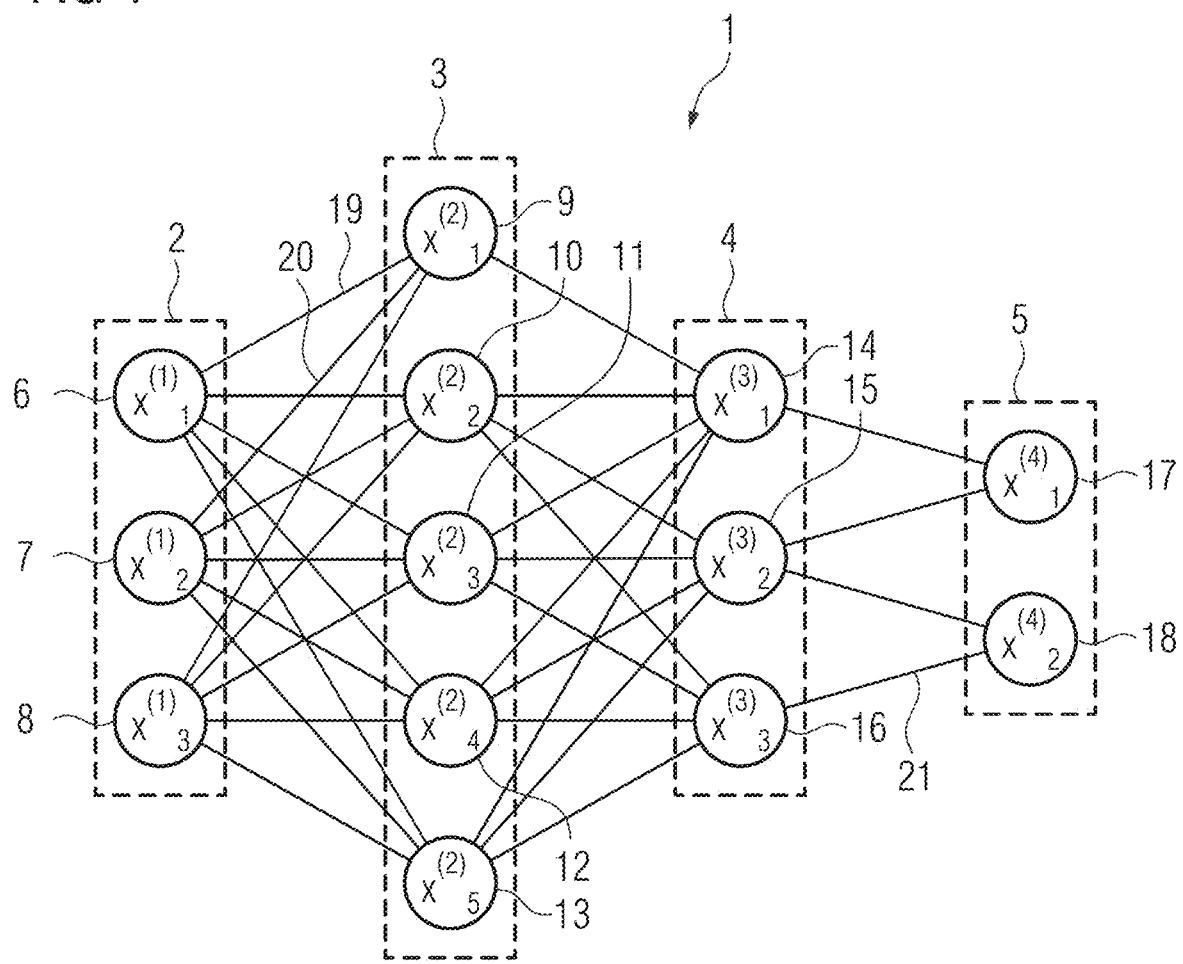
FIG. 1 shows an example embodiment of an artificial neural net.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

With a computer-implemented method of an embodiment, it is provided that the additional training data set is ascertained from the input data used during a clinical examination process with a medical imaging facility, in which the already-trained evaluation algorithm was used, and output data of the already-trained evaluation algorithm that has been at least partially correctively modified by the user.

A corrective modification by the user can, for example, be performed manually by a user of the medical imaging facility. Likewise, a corrective modification by the user can, for example, take place based on the use of a further facility or a further computer program for image analysis by a user, for example a facility or a further computer program for the automatic segmentation of image data, for the automatic quantitative evaluation of image data, etc., such as those familiar to the person skilled in the art for the analysis of medical image data.

Herein, after the training, the additional training data set can expediently become part of the basic training data for repeat runs of the method according to With a computer-implemented method of an embodiment, it is provided that the additional training data set is ascertained from the input data used during a clinical examination process with a medical imaging facility, in which the already-trained evaluation algorithm was used, and output data of the already-trained evaluation algorithm that has been at least partially correctively modified by the user.
 the invention.

According to an embodiment of the invention, it is therefore suggested that a step-by-step and seamless improvement of an artificial-intelligence evaluation algorithm be allowed in that the step-by-step improvement takes place through training during use in routine clinical practice, in particular whenever information recognized as useful in this regard arises during an examination process. For this purpose, a framework is provided together with the evaluation algorithms on the utilizing imaging facilities and at least one provider-side computing facility, which allows automated further training of evaluation algorithms based on routinely obtained clinical data. This is possible both when the artificial-intelligence evaluation algorithm is created for a specific imaging facility and only used on one specific imaging facility and also when it is used on a larger number of individual imaging facilities, wherein it is then expediently possible to ascertain additional training data sets based on clinical data from all these imaging facilities.

This in particular makes use of the fact that, in cases in which the evaluation algorithm provides satisfactory output data, there are generally no user modifications/post-corrections to the output data, but if such user changes do occur, a ground truth is already implicitly provided by the user so that the correspondingly changed output data can be used as training output data for the additional training data set. Herein, however, it should be noted that an additional training data set does not necessarily have to be created for every examination process with which a user changes output data—it is also conceivable to select examination processes for ascertaining an additional training data set with which no changes to the output data have yet been made by the user, as will be explained in more detail below.

Herein it is in particular conceivable in the context of at least one embodiment of the present invention that the further training with the additional training data set takes place each time an additional training data set is available. In this case, a continuous improvement of the evaluation algorithm is conceivable, so to speak, since each time an examination process has taken place that suggests further training and/or is suitable for further training, an improvement of the evaluation algorithm can be triggered immediately by further training. Herein, reference is made to the fact that, as will be explained in more detail below, when multiple training data sets are created during an examination process, all these training data sets will of course be used for a further training process. Alternatively, embodiments are also conceivable with which further training only takes place if a certain number, greater than 1, of additional training data sets has been collected from examination processes. Herein, in order to enable the evaluation algorithm to be improved as continuously as possible, the number is preferably selected as less than 10, in particular less than 5, for example 2 or 3.

In this way, therefore, the evaluation algorithm is continuously improved and it is generally no longer necessary to manually compile training data, in particular additional training data. Furthermore, in particular if the change to the output data, i.e. for example a correction to an annotation, already takes place on site at the imaging facility, there is no longer any need for the provider of the evaluation algorithm to generate suitable training output data. Therefore, according to the invention, a unique way is used to intelligently combine routine clinical data with machine learning in order to obtain further insights for the learning evaluation algorithm.

In general, an artificial intelligence algorithm maps cognitive functions associated with human thought processes. In particular, such an artificial intelligence algorithm is able to adapt to new circumstances through training based on training data and detect and extrapolate patterns.

In general, parameters of an artificial intelligence algorithm can be adapted through training. In particular, supervised training, semi-supervised training, reinforcement learning and/or active learning can be used for the artificial-intelligence evaluation function described here. Furthermore, it is also possible to use representation learning (an alternative expression is "feature learning"). In particular, the parameters of the artificial-intelligence evaluation algorithm can be adapted iteratively by means of multiple training steps. Incidentally, the artificial-intelligence evaluation algorithm can also be referred to as a trained evaluation function.

The evaluation algorithm can in particular comprise a neural network (neural net), a support vector machine, a decision tree and/or a Bayesian network. The evaluation algorithm can furthermore be based on k-means clustering, Q-learning, genetic algorithms and/or assignment rules. In the context of the present invention, the artificial-intelligence evaluation algorithm preferably comprises a neural net. The neural net can be a deep neural net, a convolutional neural network (CNN) or a deep CNN. Furthermore, the neural net can be an adversarial network, a deep adversarial network and/or a generative adversarial network (GAN). In particular, herein, neural nets can be understood to be a sequence of layers, representing abstractable intermediate steps.

In the context of at least one embodiment of the present invention, the imaging facility can in particular be an X-ray facility, for example a computed tomography facility or a magnetic resonance facility. Herein, a large number of evaluation algorithms have been proposed, in particular in the field of computed tomography, to which the training method of at least one embodiment of the present invention can be applied. Of course, it is also possible to consider image data from other imaging facilities, for example from ultrasound imaging facilities, PET imaging facilities and the like.

With regard to the evaluation algorithm, it can be provided that the output data itself is used to control at least one medical technical facility, in particular the medical imaging facility with which the image data that was changed as input data was recorded. This means that the evaluation algorithm can be used to map the often complex process of deriving suitable control parameters/control data for further automatically performed processes in order here to achieve significant support for users and to significantly increase the efficiency of examination processes and/or treatment processes. Improving the evaluation algorithm by means of the at least substantially continuous further training suggested here significantly reduces the number of cases requiring reworking/corrections, automation is expedited and the examination and/or treatment time is reduced. In particular, in this context it can be provided that the output data can at least partially control a further imaging process of the imaging facility. Thus, the image data that serves as input data can, for example, be image data of an overview image and/or another preliminary recording; furthermore, the image data can be part of a recording sequence with which images of one step of the sequence can influence the recording of images in further steps of the sequence.

In one specific embodiment, it can, for example, be provided that the output data describes a region of interest to be used in particular as a recording region for a further imaging process and/or comprise a segmentation of an anatomical feature. For example, with respect to computed tomography, artificial-intelligence evaluation algorithms have already been suggested that evaluate overview recordings of a patient and fully automatically determine the optimal positioning of the patient for the computed tomography recording, the optimal selection of a recording region and the optimal radiation doses by means of artificial intelligence. Herein, the medical imaging facility can in particular also comprise a 3D camera from which the image data, in particular to complement computed tomography-image data, can at least partially originate. Herein, in this context reference is made once again to the fact that the examples named can also represent only partial aspects of the artificial-intelligence evaluation algorithm, for example in respect of fully automated imaging facility assistance, such as is known, for example by the name FAST—"fully assisting scanner technologies".

Especially in the case of output data used hereinafter for control, this data is frequently displayed or visualized to the user, so that the user can either confirm it or change it again, which can lead to the aforementioned changed output data. If, for example, the scanner defines a recording region (field of view) that should contain a specific organ, but this organ is not completely contained therein, the recording region can be enlarged accordingly and the like by the user. Segmentation results can, for example, be post-corrected.

In addition to such controlling output data, the invention also covers applications in which the output data comprises evaluation data to be used as the basis for a diagnosis, in particular an anatomical and/or functional score. In this context, therefore, the diagnosis to be performed by the physician can be supported by means of the evaluation algorithm, wherein here once again the physician usually also inspects and analyzes the underlying image data and can, therefore, take corrective action if necessary, i.e. change the output data.

With regard to the location at which the further training process takes place, there are various possibilities in the context of at least one embodiment of the present invention. For example, it can be provided in a first embodiment of the present invention that the further training is performed by a computing facility assigned to the imaging facility, in particular a computing facility of the imaging facility, wherein the further-trained evaluation algorithm is transferred to a computing facility of the provider of the evaluation algorithm, in particular the manufacturer of the imaging facility, via a communication link. Therefore, the evaluation algorithm can be further trained directly in a clinical facility in which the imaging facility is also arranged. In this way, data protection, which is in principle relevant for such clinical data, is significantly simplified since patient-related data from the examination process itself does not have to leave the clinical facility. Nevertheless, in this case it is again expedient to transmit the further-trained evaluation algorithm to the provider, which may correspond to the manufacturer of the imaging facility, for example so that it can be validated there and if applicable released, in particular also to other clinical facilities/imaging facilities.

In another embodiment of the present invention, it can be provided that the additional training data set and/or the ascertaining data used to ascertain the additional training data set is or are transferred via a communication link to a computing facility of the provider of the evaluation algorithm, in particular the manufacturer of the imaging facility, where the further training takes place. Herein, ascertaining data can in particular comprise input data and/or output data of the application of the evaluation algorithm and/or ascertaining data derived therefrom. In this case, therefore, the further training takes place at the location of the provider of the evaluation algorithm using at least one computing facility, which can in particular also be part of a cloud environment.

In this context, a particularly advantageous development of at least one embodiment of the present invention provides that the additional training data set and/or the ascertaining data are preprocessed for anonymization prior to being transferred to the provider-side computing facility. In this way, a contribution to data protection can be made in that the patient's personal data is protected to the greatest degree possible. Herein, it can be provided in a first specific embodiment that the image data is restricted to a sub-region relevant for the evaluation algorithm's evaluation and/or that personal information about the person recorded is removed. For example, it is therefore conceivable that only a part of the image data, restricted to absolutely necessary body regions, is transmitted, for example only the liver region.

However, in one particularly advantageous embodiment of the present invention, it can be provided that the portion of the evaluation algorithm to be further trained is restricted as unchangeable by defining at least one first layer of the evaluation algorithm, wherein the original input data already processed by the at least one first layer of the evaluation algorithm is ascertained as training input data and transmitted to the provider-side computing facility. This means that the image data is not provided per se or in unprocessed form, but is ultimately anonymized by passing it through at least one layer of the evaluation algorithm, which is in particular embodied as a neural net, i.e. certain extracted image characteristics are used instead of the original image data. The correspondingly used layers, which mainly target low levels of image characteristic extraction, then remain unchanged in the training, so that only deeper layers are updated. In this way, abstracted and anonymized training input data is generated in a simple manner without any relevant loss of data, but can nevertheless be used directly as training input data for the evaluation algorithm, in that it is simply fed in after the at least one defined first layer.

In general terms, the further-trained evaluation algorithm can then in turn be provided by the provider to the respective imaging facilities that use it. Herein, in the context of the present invention, it is preferable for the further-trained evaluation algorithm only to be provided after an assessment on the provider-side computing facility for application at least on the imaging facility from which the additional training data set originates, in particular on all imaging facilities using the evaluation algorithm, wherein an assessment score is ascertained for the assessment by the provider-side computing facility. This means an assessment process can decide the extent to which the further-trained evaluation algorithm is provided as an update to different imaging facilities. This can, in particular when training is to be carried out specifically for one specific imaging facility, in certain cases, explicitly only refer to this specific imaging facility. In many cases, however, it may be more advantageous if, just as additional training data sets from different imaging facilities or the training results thereof can be merged, the improvement is made for all imaging facilities using the evaluation algorithm. Overall, it may therefore be said that the evaluation algorithm on the clinical system is only updated if a sufficiently significant improvement of the evaluation algorithm has occurred as a result of the further machine learning. Herein, in principle, it is possible to used common assessment metrics or assessment scores that are known in principle, for example the "area under the curve" (AUC) and/or the F1 score.

The evaluation quality of such assessment scores is generally checked using special test data (validation data). Herein, test data sets (validation data sets) comprise test input data and test output data that describe the ground truth, wherein these test data sets are deliberately not used as training data sets, i.e. they are kept as test cases for the trained evaluation algorithm in order to be able to check its evaluation process also with regard to cases that have not already been included in the training.

In this context, one embodiment of the present invention can also provide that the provider-side computing facility applies the further-trained evaluation algorithm to test data comprising test sets with test input data and test output data and evaluates it by comparing the output data ascertained with the test input data by the further-trained evaluation algorithm with the respective test output data for ascertaining the assessment score.

Herein, it is also quite conceivable to ascertain test data sets from potential additional training data sets. For example, an expedient development of the present invention provides that, in the case of the transfer of the additional training data sets and/or the ascertaining data to the provider-side computing facility, if multiple additional training data sets are ascertained and a suitability condition is met, at least one of the ascertained additional training data sets is not used for further training but is redeclared as a test data set and added to the test data. In this way, it is, therefore, possible to improve not only the training basis of the evaluation algorithm, but also its validation basis, for example by branching off some cases described by the suitability criterion that are fundamentally difficult to appraise in order to add them to the test data and thus also to enable a development with regard to validation.

In one specific embodiment of the present invention, it can be provided that the further-trained evaluation algorithm is provided when an improvement threshold for the improvement of the assessment score is exceeded. It is therefore possible to define which improvement of the evaluation algorithm is considered to be sufficiently significant for the evaluation algorithm to be updated in the clinical application. It can furthermore be provided that the provision of the further-trained evaluation algorithm is deferred or even discarded in the event of a deterioration of the assessment score. In very rare cases, it can happen that, as an unwanted effect, there is even a deterioration of the general performance of the evaluation algorithm in which case an update does not appear to make sense.

As already mentioned, in the context of at least one embodiment of the present invention, the selection of examination processes from which a new additional training data set is to be generated, takes place at least largely, preferably completely, automatically. In this way, manual selection of training data sets is no longer necessary.

In one specific advantageous embodiment in this regard, it can be provided that, to select an examination process for ascertaining an additional training data set,
examination processes are selected with output data of the evaluation algorithm that has been changed by a user, and/or,
if the evaluation algorithm outputs an uncertainty measure assigned to the output data describing the uncertainty in the ascertainment of the output data, the examination process is selected when an uncertainty threshold for the uncertainty measure is exceeded, and/or
a first similarity measure for at least the input data with default case class input data describing a case class with a high degree of uncertainty and/or failure rate for the evaluation algorithm is ascertained and the examination process is selected when a selection threshold is exceeded by the similarity measure.

In particular, therefore, there can be different, also cumulatively usable, possibilities for the selection of examination processes, i.e. cases to be added to the training data are available. A first option relates to the selection of examination processes with which the output data was changed by the user, for example during the imaging data recording with the imaging facility itself or, however, during the diagnosis. As has already been explained, such changes by the user indicate that the ground truth deviates to a greater or lesser degree from the evaluation result described by the output data. Accordingly, the user-corrected, i.e. changed, output data, can be considered to be the ground truth and a new additional training data set is created in a natural way. With this first option, of course, an additional selection can take place, for example the strength of the changes to the output data can be evaluated and/or, in particular in combination with the second option, the potential for improvement can be appraised.

The second option relates to the automatic selection of cases based on an uncertainty measure, which the evaluation algorithm likewise outputs for routine clinical cases. For example, cases in which a high uncertainty measure is output, i.e. a high uncertainty with respect to the evaluation result described by the output data is assumed, can be selected automatically in order to determine an additional training data set.

Finally, in a third option there can also be a targeted query for cases. If, for example, classes of cases are known in which failures, errors or high degrees of uncertainty frequently occur, such case classes can be provided to the respective imaging facilities, for example, as at least one set of case class input data belonging to the case class. With regard to this case class input data, a similarity measure of the currently used input data, i.e. in particular the image data with respect to one another, can be determined completely automatically in order to define whether or not the current examination process falls into this case class. Therefore, extremely similar cases can be collected automatically and in a targeted manner in order to obtain additional training data sets that are specifically aimed at improving the case class. Of course, this third option can be combined with the first option.

It should also be noted at this point that different specific similarity measures known in principle in the prior art can be used, in particular when comparing image data, also similarity measures that can be used specially for image data. Similarity measures that can be used in the context of the present invention include, for example, k-means clustering, gray-scale value differences, random forest measures and/or also machine-learned similarity measures tailored to a specific question.

In particular with regard to the above-discussed second and third option, but also for further conceivable options for automatic selection, it may happen that the user has not yet changed the output data for a selected examination process. In this case, an expedient embodiment of the present invention can provide that a prompt to check and correct the output data is output to at least one user, wherein the output data changed in response thereto is used as training output data. A corresponding output can already take place in the clinical facility in which the imaging facility is used and therefore address a user there, in particular a physician there, who is asked to appraise the output data of the evaluation algorithm in order to improve it. However, it is also possible that, in particular during the transmission of ascertaining data to the provider-side computing facility, a user is consulted by the provider in order to appraise the actual output data and adapt it accordingly with regard to the ground truth. Herein, however, reference is made to the fact, with regard to the nature of the cases addressed in the second and third option, that such cases are likely to be rare anyway so that subsequent manual input can be kept at an extremely low level.

Reference is made to the fact that it is also conceivable, in the context of at least one embodiment of the present invention, optionally to obtain alternative information to be used as training output data in some other way, for example by using alternative algorithms that are more robust, but are not conceivable in clinical operation, for example due to a very long runtime, for example highly complex simulations and the like.

The approach described in the context of at least one embodiment of the present invention can also comprise quality assurance with regard to the additional training data sets. There are also various possibilities for this which can be used in a complementary manner, if necessary.

In a first possibility in this regard, it can be provided that, for quality assurance purposes, the changed output data to be used as training output data sets is only used when user confirmation is available. This means the user can be prompted to confirm the image data and the quality of the output data that the user has in particular already changed for each case that is to be added to the training data. Such a prompt can, for example, be requested if the examination process has ended.

In a second possibility, it can be provided that the selection of the examination processes is modified to avoid or even establish bias with regard to a specific case class. This means, with the automatic selection of cases that are to be used for training, specific care can be taken to avoid bias with regard to a specific case class, as is known in principle in the prior art with regard to unbalanced training data sets. However, in some cases it may also be conceivable to enforce bias, for example, if the underlying training was already unbalanced or a new case class is added, see also the above-discussed second and third option.

A further generally applicable approach to quality assurance, i.e. a third possibility, that is particularly preferred provides that, at the conclusion of the ascertainment of the additional training data set, at least one second similarity measure of the potential additional training data set ascertained, in particular the input data and the in particular user-changed output data, is ascertained with training data sets of the basic training data, wherein, if the maximum similarity measure falls below a verification threshold, the potential additional training data set is marked for checking by a human expert and stored for this checking. It is only after this check that the additional training set, adapted by the expert if necessary, is used for further training or even discarded. In other words, similarity measures for already confirmed training data sets can be ascertained, wherein, for example, the aforementioned similarity measures can be used. If there is only a low maximum similarity, it may be expedient to have this potential additional training data set checked again by an expert before it can be added to the training data.

In the context of at least one embodiment of the present invention, some approaches for ensuring or increasing the robustness of the evaluation algorithm with regard to various reconstruction methods are also conceivable. More complex, in particular tomographic, imaging techniques generally use a reconstruction process in order to ascertain image data from raw data, i.e. the directly measured information, which can be output as an image to a user. For example, in computed tomography a three-dimensional image data set is reconstructed from two-dimensional projection images, for example by means of filtered back projection or iterative reconstruction (algebraic reconstruction). Similarly, in magnetic resonance imaging, raw data is back-projected from k-space to image space in order to generate image data sets.

It can be provided in a first approach of this kind with regard to the reconstructions that the evaluation algorithm assumes a default reconstruction of the raw data obtained with the imaging facility to form the image data by at least one default reconstruction parameter, wherein the reconstruction is performed by the image recording facility independently of a user reconstruction and the image data ascertained by the default reconstruction is used as training input data. In other words, the robustness of the evaluation algorithm can be increased in that a default, so to speak standardized, reconstruction technique with default reconstruction parameters is in principle used to generate the image data of the input data. Regardless of whether a user now desires the reconstruction of an image with other reconstruction parameters for a specific examination process, the default reconstruction with the default reconstruction parameters can in any case additionally take place on the imaging facility or the imaging facility-side computing facility in order to provide the correct input data for the evaluation algorithm. In this way, no different types of reconstruction, i.e. variations of the reconstruction that led to the image data, have to be taken into account in the training process of the evaluation algorithm and this can improve the robustness of the training and hence also the quality of the output data.

However, in an alternative, second, likewise advantageous approach, it can also be provided that, in addition to a user-requested reconstruction of the raw data obtained with the imaging facility to form the image data used as input data, at least one further default reconstruction of the raw data to form further image data takes place, wherein the further image data is used as training input data for further additional training data sets using the same training output data as for the additional training data set using the input data. In other words, it can be provided, to ensure the robustness of the evaluation algorithm with regard to reconstruction parameters, that additional reconstructions of the raw data of the examination process are provided in order in this regard to increase the bandwidth provided for training in the additional training data sets. In this case, multiple additional training data sets can be compiled with regard to an examination process. With regard to this completely automatic performance of further reconstruction processes, it should also be noted that these are possible since, at the point in time at which an examination process is selected for ascertaining an additional training data set, the raw data is usually still present on the imaging facility and has not yet been automatically deleted.

In other words, to summarize these approaches, it can be stated that, due to the fact that the training data sets are ascertained immediately during or after the examination process, the raw data of the imaging process are still available, so that targeted automatic reconstructions can be performed in order to allow or ensure robustness with respect to different reconstruction parameters or the standardization of the evaluation algorithm with regard to the reconstruction parameters.

In addition to the method, at least one embodiment of the present invention also relates to a training system having at least one medical imaging facility with a computing facility assigned to the imaging facility, which is embodied to execute an artificial-intelligence evaluation algorithm that has already been trained based upon basic training data, which ascertains output data describing evaluation results from input data comprising image data recorded with the medical imaging facility, and a computing facility provided by the provider of the evaluation algorithm, which is connected to the at least one imaging facility-side computing facility via a communication link, wherein the computing facilities comprise:
 an ascertaining unit for ascertaining at least one additional training data set containing training input data and training output data assigned thereto, and
 a training unit for training the evaluation algorithm using the at least one additional training data set,
 wherein the ascertaining unit is embodied to ascertain the additional training data set from the input data used during a clinical examination process with a medical imaging facility, in which the already-trained evaluation algorithm was used, and output data of the already-trained evaluation algorithm that has been at least partially correctively modified by the user.

All statements with regard to the method according to at least one embodiment of the invention can be transferred analogously to the training system according to at least one embodiment of the invention with which, therefore, the advantages already named can likewise be obtained. In particular, the computing facilities can contain at least one processor and/or at least one storage means for forming functional units. The imaging facility-side computing facility can be integrated into the imaging facility itself, for example form a control facility of the same. Herein, the evaluation algorithm can, for example, be implemented in an image-processing unit or the like. The at least one imaging facility-side computing facility and/or the at least one provider-side computing facility can in each case be part of a cloud, in particular also as multiple computing facilities.

The training system according to at least one embodiment of the invention can furthermore comprise an input and/or output unit. The input and/or output unit can be embodied for direct operation by a user (for example, screen, keyboard, touch display) or it can also be embodied as a hardware or software interface (for example PCI bus, USB or Firewire).

A computer program according to at least one embodiment of the invention can, for example, be loaded directly into storage means of the computing facilities of a training system according to at least one embodiment of the invention and has program segments for executing the steps of a method according to at least one embodiment of the invention when the computer program is executed in the computing facilities of the training system. The computer program can be stored on an electronically readable data carrier according to at least one embodiment of the invention, which therefore comprises electronically readable control information stored thereon, which comprises at least one computer program according to at least one embodiment of the invention and is embodied such that, when the data carrier is used in a training system according to at least one embodiment of the invention, it performs a method according to at least one embodiment of the invention.

A storage means can be implemented as a non-permanent main memory (random access memory, RAM for short) or as a permanent mass storage facility (hard disk, USB stick, SD card, solid state disk).

Therefore, as already explained in the introduction, the computer program provides a framework which allows at least substantially continuous further learning of the evaluation algorithm based upon the actual routine clinical cases. For this purpose, program parts of the computer program according to at least one embodiment of the invention can be provided on the imaging facility-side computing facility and the provider-side computing facility, which means that the computer program according to at least one embodiment of the invention can in particular be executed in a distributed manner in the training system.

FIG. 1 shows an example embodiment of an artificial neural net 1. Other terms for the artificial neural net 1 are "artificial neural network" "neural network" or "neural net".

The artificial neural network 1 comprises nodes 6 to 18 and edges 19 to 21, wherein each edge 19 to 21 is a directed connection from a first node 6 to 18 to a second node 6 to 18. In general, the first node 6 to 18 and the second node 6 to 18 are different nodes 6 to 18, but it is also conceivable for the first node 6 to 18 and the second node 6 to 18 to be identical. For example, in FIG. 1 the edge 19 is a directed connection from the node 6 to the node 9 and the edge 21 is a directed connection from the node 16 to the node 18. An edge 19 to 21 from a first node 6 to 18 to a second node 6 to 18 is referred to as an ingoing edge for the second node 6 to 18 and as an outgoing edge for the first node 6 to 18.

In this example embodiment, the nodes 6 to 18 of the artificial neural net 1 can be arranged in layers 2 to 5, wherein the layers can have an intrinsic order introduced by the edges 19 to 21 between the nodes 6 to 18. In particular edges 19 to 21 can only be provided between adjacent layers of nodes 6 to 18. In the example embodiment depicted, there is an input layer 110 that only has the nodes 6, 7, 8 in each case without an ingoing edge. The output layer 5 only comprises the nodes 17, 18, in each case without outgoing edges, wherein furthermore there are hidden layers 3 and 4 between the input layer 2 and the output layer 5. Generally, the number of hidden layers 3, 4 can be selected as desired. The number of nodes 6, 7, 8 of the input layer 2 usually corresponds to the number of input values into the neural network 1, and the number of nodes 17, 18 in the output layer 5 usually corresponds to the number of output values of the neural network 1.

In particular, a (real) number can be assigned to the nodes 6 to 18 of the neural network 1. Herein, $x^{(n)}_i$ denotes the value of the ith node 6 to 18 of the nth layer 2 to 5. The values of the nodes 6, 7, 8 of the input layer 2 are equivalent to the input values of the neural network 1, while the values of the nodes 17, 18 of the output layer 5 are equivalent to the output values of the neural network 1. In addition, each edge 19, 20, 21 can be assigned a weight in the form of a real number. In particular, the weight is a real number in the interval $[-1, 1]$ or the interval $[0, 1,]$. Herein, $w^{(m,n)}_{i,j}$ denotes the weight of the edge between the ith nodes 6 to 18 of the mth layer 2 to 5 and the jth nodes 6 to 18 of the nth layer 2 to 5. Furthermore, the abbreviation $w^{(n)}_{i,j}$ is defined for the weight $w^{(n,n+1)}_{i,j}$.

In order to calculate output values of the neural net 1, the input values are propagated by the neural net 1. In particular, the values of the nodes 6 to 18 of the (n+1)th layer 2 to 5 can be calculated based on the values of the nodes 6 to 18 of the nth layer 2 to 5 by $$x_j^{(n+1)} = f(\Sigma_i x_i^{(n)} \cdot w_{i,j}^{(n)}).$$

Herein f is a transfer function, which can also be referred to as an activation function. Known transfer functions are step functions, sigmoid functions (for example the logistic function, the generalized logistic function, the hyperbolic tangent, the arctangent, the error function, the smooth step function) or rectifier functions. The transfer function is substantially used for normalization purposes.

In particular, the values are propagated layer-by layer by the neural net 1, wherein values of the input layer 2 are defined by the input data of the neural net 1. Values of the first hidden layer 3 can be calculated based on the values of the input layer 2 of the neural net 1, values of the second hidden layer 4 can be calculated based on the values in the first hidden layer 3, etc.

In order to be able to establish the values $w_{i,j}^{(n)}$ for the edges 19 to 21, the neural net 1 has to be trained using training data. In particular, training data comprise training input data and training output data, hereinafter referred to as $t_i$. For a training step, the neural network 1 is applied to the training input data in order to ascertain calculated output data. In particular, the training output data and the calculated output data comprise a number of values, wherein the number is determined as the number of nodes 17, 18 of the output layer 5.

In particular, a comparison between the calculated output data and the training output data is used to adapt the weights recursively within the neural net 1 (back propagation algorithm). In particular, the weights can be changed according to $$w'^{(n)}_{i,j} = w^{(n)}_{i,j} - \gamma \cdot \delta_j^{(n)} \cdot x_i^{(n)},$$

wherein γ is a learning rate and the numbers $\delta_j^{(n)}$ can be calculated recursively as $$\delta_j^{(n)} = (\Sigma_k \delta_k^{(n+1)} \cdot w_{j,k}^{(n+1)}) \cdot f'(\Sigma_i x_i^{(n)} \cdot w_{i,j}^{(n)})$$

based on $\delta_j^{(n+1)}$ when the (n+1)th layer is not the output layer 5, and $$\delta_j^{(n)} = (x_k^{(n+1)} - t_j^{(n+1)}) \cdot f'(\Sigma_i x_i^{(n)} \cdot w_{i,j}^{(n)})$$

if the (n+1)th layer is the output layer 5, wherein f' is the first derivative of the activation function and $y_j^{(n+1)}$ is the comparative training value for the jth node 17, 18 of the output layer 5.

An example of a convolutional neural network (CNN) is also provided below with regard to FIG. 2. Herein, it should be noted that the term "layer" is used there in a slightly different way than for classical neural nets. For a classical neural net, the term "layer" only refers to the set of nodes that forms a layer, i.e. a specific generation of nodes. For a convolutional neural network, the term "layer" is often used as an object that actively changes data, in other words as a set of nodes of the same generation and the set of either incoming or outgoing edges.

Figure 2:
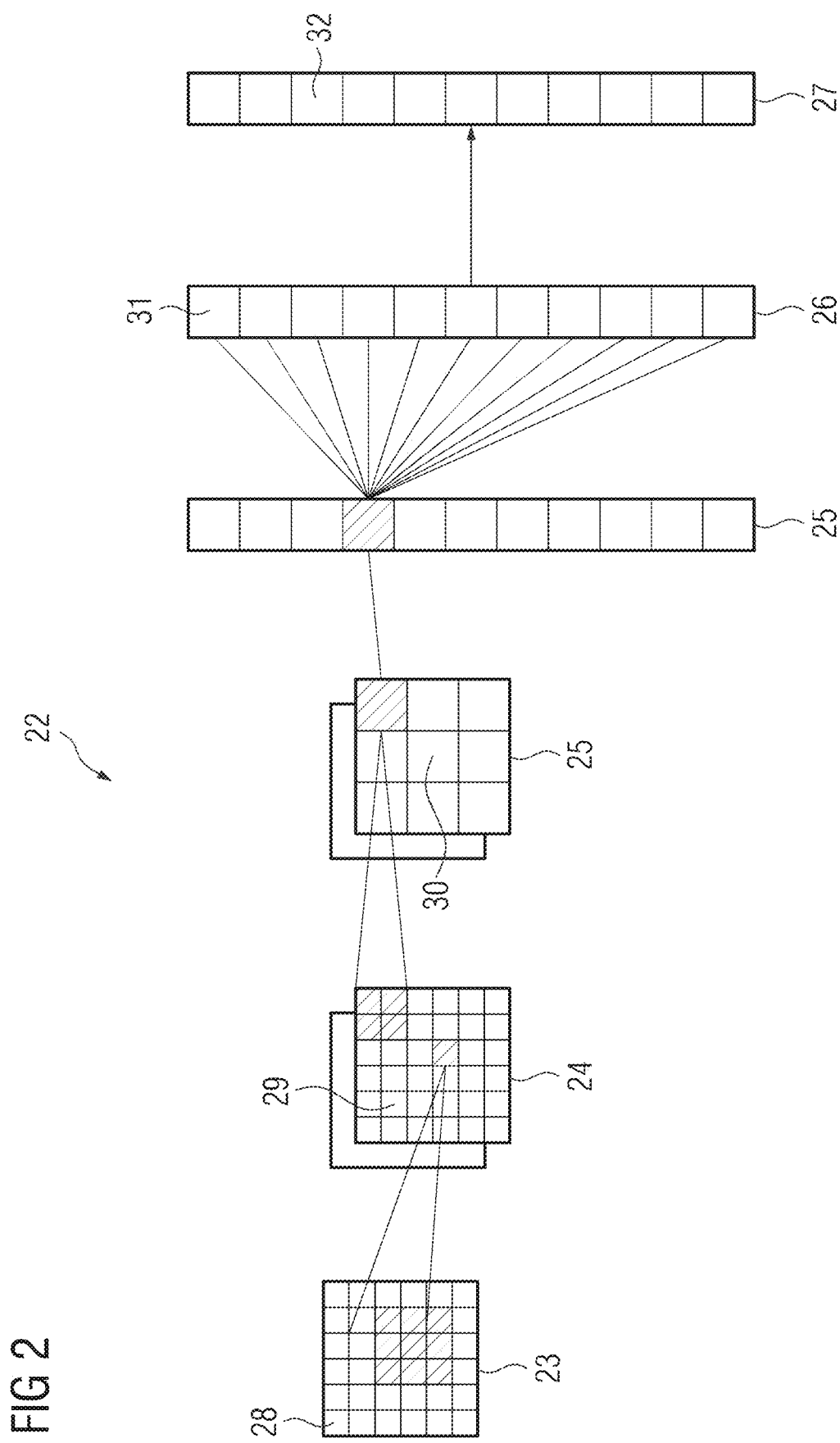
FIG. 2 shows an example embodiment of a convolutional neural network (CNN)

FIG. 2 shows an example embodiment of a convolutional neural network 22. In the example embodiment depicted, the convolutional neural network 22 comprises an input layer 23, a convolutional layer 24, a pooling layer 25, a completely connected layer 26 and an output layer 27. In alternative embodiments, the convolutional neural network 22 can comprise multiple convolutional layers 24, multiple pooling layers 25 and multiple fully connected layers 26, as well as other types of layers. The sequence of layers can be selected as desired, wherein fully connected layers 26 usually form the last layers before the output layer 27.

In particular, within a convolutional neural network 22, the nodes 28 to 32 in one of the layers 23 to 27 can be understood as being arranged in a d-dimensional matrix or as a d-dimensional image. In particular, in the two-dimensional case, the value of a node 28 to 32 with the indices i, j in the nth layer 23 to 27 may be designated $x^{(n)}[i,j]$.

Reference should be made to the fact that the arrangement of the nodes 28 to 31 in a layer 23 to 27 has no effect on the calculations within the convolutional neural network 22 as such, since these effects are defined exclusively by the structure and weights of the edges.

A convolutional layer 24 is in particular characterized by the fact that the structure and weights of the ingoing edges form a convolution operation based on a specific number of kernels. In particular, the structure and weights of the ingoing edges can be selected such that the values $x_k^{(n)}$ of the nodes 29 of the convolutional layer 24 are ascertained as a convolution $x_k^{(n)} = K_k * x^{(n-1)}$ based on the values $x^{(n-1)}$ of the nodes 28 of the preceding layer 23, wherein, in the two-dimensional case, the convolution * can be defined as $$x_k^{(n)}[i,j] = (K_k * x^{(n-1)})[i,j] = \Sigma_i \Sigma_j K_k[i',j'] \cdot x^{(n-1)}[i-i',j-j'].$$

Here, the kth kernel $K_k$ is a d-dimensional matrix, in this example embodiment a two-dimensional matrix, which is usually small compared to the number of nodes 28 to 32, for example a 3×3 matrix or a 5×5 matrix. In particular, this implies that the weights of the ingoing edges are not independent, but are selected such that they generate the above convolution equation. In the example of a kernel forming a 3×3 matrix, there are only nine independent weights (wherein each entry in the kernel matrix corresponds to an independent weight) regardless of the number of nodes 28 to 32 in the corresponding layer 23 to 27. In particular, for a convolutional layer 24 the number of nodes 29 in the convolutional layer 24 is equivalent to the number of nodes 28 in the preceding layer 23 multiplied by the number of convolutional kernels.

If the nodes 28 in the preceding layer 23 are arranged as a d-dimensional matrix, the use of the plurality of kernels can be understood to be the addition of a further dimension, which is also referred to as a depth dimension, so that the nodes 29 in the convolutional layer 24 are arranged as a (d+1)-dimensional matrix. If the nodes 28 of the preceding layer 23 are already arranged as a (d+1)-dimensional matrix with a depth dimension, the use of a plurality of convolutional kernels can be understood as an expansion along the depth dimension, so that the nodes 29 of the convolutional layer 24 are equally arranged as a (d+1)-dimensional matrix, wherein the size of the (d+1)-dimensional matrix in the depth dimension is greater than in the preceding layer 23 by the factor formed by the number of kernels.

The advantage of using convolutional layers 24 is that the spatially local correlation of the input data can be utilized in that a local connection pattern is created between nodes of adjacent layers, in particular in that each node only has connections to a small region of the nodes in the preceding layer.

In the example embodiment depicted, the input layer 23 comprises thirty-six nodes 28 arranged as a two-dimensional 6×6 matrix. The convolutional layer 24 comprises seventy-two nodes 29 arranged as two two-dimensional 6×6 matrices, wherein each of the two matrices is the result of a convolution of the values of the input layer 23 with a convolutional kernel. In the same way, the nodes 29 of the convolutional layer 24 can be understood as being arranged in a three-dimensional 6×6×2 matrix, wherein the last-mentioned dimension is the depth dimension.

A pooling layer 25 is characterized in that the structure and weights of the ingoing edges and the activation function of its nodes 30 define a pooling operation based on a non-linear pooling function f. For example, in the two-dimensional case, the values $x^{(n)}$ of the nodes 30 in the pooling layer 25 can be calculated based on the values $x^{(n+1)}$ of the nodes 29 of the preceding layer 24 as $$x^{(n)}[i,j] = f(x^{(n-1)}[id_1, jd_2], \ldots, x^{(n-1)}[id_1+d_1-1, jd_2+d_2-1]).$$

In other words, the use of a pooling layer 25 can reduce the number of nodes 29, 30 in that a number of d1×d2 of adjacent nodes 29 in the preceding layer 24 are replaced by one single node 30 calculated as a function of the values of said number of adjacent nodes 29. In particular, the pooling function f can be a maximum function, an averaging or the L2 norm. In particular, for a pooling layer 25, the weights of the ingoing edges can be fixed and cannot be modified by training.

The advantage of using a pooling layer 25 is that the number of nodes 29, 30 and the number of parameters is reduced. This leads to a reduction in the number of calculations required within the convolutional neural network 22 and hence to control of overfitting.

In the example embodiment depicted, the pooling layer 25 is a max pooling layer in which four adjacent nodes are replaced by one single node the value of which is formed by the maximum of the values of the four adjacent nodes. Max pooling is applied to each d-dimensional matrix of the previous layer; in this example embodiment, max pooling is applied to each of the two two-dimensional matrices so that the number of nodes is reduced from seventy-two to eighteen.

A fully connected layer 26 is characterized in that a plurality of, in particular all, edges are present between the nodes 30 of the previous layer 25 and the nodes 31 of the fully connected layer 26, wherein the weight of each of the edges can be adapted individually. In this example embodiment, the nodes 30 of the preceding layer 25 and the fully connected layer 26 are shown as both two-dimensional matrices and as non-contiguous nodes (depicted as a row of nodes, wherein the number of nodes has been reduced for purposes of better illustration). In this example embodiment, the number of nodes 31 in the fully connected layer 26 is equal to the number of nodes 30 in the preceding layer 25. In alternative embodiments, the number of nodes 30, 31 may differ.

In addition, in this example embodiment, the values of the nodes 32 in the output layer 27 are determined by applying the softmax function to the values of the nodes 31 in the preceding layer 26. The application of the softmax function causes the sum of the values of all nodes 32 in the output layer 27 to be one and all values of all nodes 32 in the output layer to be real numbers between 0 and 1. If the convolutional neural network 22 is used to classify input data, in particular the values of the output layer 27 can be interpreted as the probability of the input data falling into one of the different classes.

Likewise, a convolutional neural network 22 can have a ReLU layer, wherein ReLU means "rectified linear units". In particular, the number of nodes and the structure of the nodes within a ReLU layer is equivalent to the number of nodes and the structures of the nodes in the preceding layer. The value of each node in the ReLU layer can in particular be calculated by applying a rectifier function to the value of the corresponding node in the preceding layer. Examples of rectifier functions are $f(x)=\max(0,x)$, hyperbolic tangent or the sigmoid function.

Convolutional neural networks 22 can in particular be trained based on the back propagation algorithm. Overfitting can be avoided by applying regularization methods, for example dropout of individual nodes 28 to 32, stochastic pooling, use of artificial data, weight decay based on the L1 or L2 norm or maximum norm restrictions.

Figure 3:
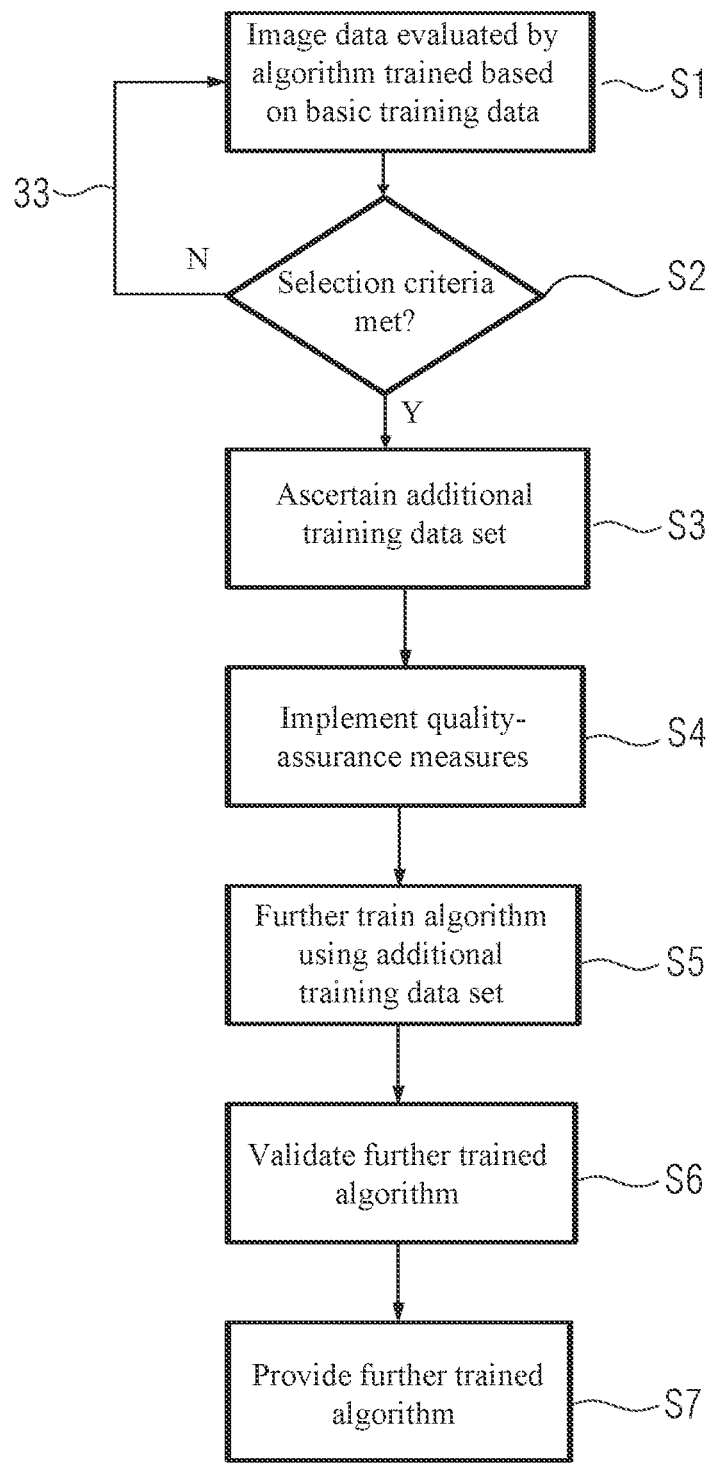
FIG. 3 shows an example flow diagram of the method according to an example embodiment of the invention.

FIG. 3 shows a flow diagram of an example embodiment of the method according to the invention. There, in step S1, the process of the examination of a patient with an imaging facility, for example a computed tomography facility, takes place. Herein, as is known in principle, raw data, for example two-dimensional projection images, are recorded, whereupon image data, for example a three-dimensional image data set, is reconstructed from the raw data. In step S1, this image data is also evaluated by an artificial-intelligence evaluation algorithm that has already been trained using basic training data. The artificial-intelligence evaluation algorithm uses as input data at least the just addressed image data, evaluates this data and accordingly provides output data describing the evaluation result. For example, the evaluation algorithm can ascertain control data for a further imaging process within the examination process. Such control data can, for example, relate to the recording region, the strength of the X-ray radiation and the like. In other embodiments or as an additional evaluation algorithm, the output data can also comprise image-related evaluation results to be used as a basis for diagnosis and/or therapy. With regard to therapy, control data may also arise here.

In each case a user, for example a treating physician and/or another trained operator of the imaging facility, receives a display of the image data and the evaluation results, i.e. the output data, for example in the case of a recording region, visualized within the image data. The user can now appraise the quality of the output data of the artificial-intelligence evaluation algorithm and, for example, make corrective changes, so that in this case user-changed output data can arise.

The artificial-intelligence evaluation algorithm considered here by way of example has a neural net with multiple layers. Herein, the first layers through which the input data passes are used to extract image characteristics (image features). For example, the first layers of the neural net of the evaluation algorithm that are passed-through can represent an encoder.

In the method according to an embodiment of the invention, the artificial-intelligence evaluation algorithm is to be improved by further training. Additional training data sets to be used for further training, which after use for further training can become part of the basic training data with regard to further runs of the method according to the invention, should be determined based upon routine clinical examination processes such as those performed in step S1. Consequently, in step S2, a check is performed as to whether the examination process meets selection criteria, i.e. should be used to ascertain an additional training data set. If this is not the case, the method returns to step S1 as indicated by the arrow 33.

In the context of an embodiment of the present invention, there are multiple options for the selection of examination processes in order to compile additional training data sets, which can also be applied in a mutually complementarily manner. In a first option, one selection criterion can check whether, as described, the output data of the evaluation algorithm has actually been changed by a user. This indicates that the evaluation deviates from the ground truth. However, in a second option, a selection criterion can also automatically check whether an uncertainty measure likewise output by the evaluation algorithm exceeds an uncertainty threshold. Such an uncertainty measure estimates the intrinsic uncertainty in the ascertainment of the output data.

If the uncertainty measure exceeds the uncertainty threshold, i.e. there is a high degree of uncertainty, it is advisable to use the clinical data of the examination process as an additional training data set, since here there is evidently great potential for improving the evaluation algorithm.

In a third option in the context of a selection criterion, a first similarity measure can be ascertained between the input data used in step S1, which comprises the image data, and at least one set of case class input data. Here, in particular the corresponding image data is compared. The case class input data is representative of a case class of applications to be processed by the evaluation data set, i.e. it represents at least one case of this case class. The corresponding case class is a case class with which there is a high degree of uncertainty and/or even failure rate for the evaluation algorithm, i.e. a class of cases with which the evaluation algorithm has difficulties. Therefore, the first similarity measure describes how similar the application considered in the current examination process is to this case class. If the similarity is high, i.e. if a selection threshold is exceeded by the first similarity measure, the current examination process can be selected in order also to be able to particularly improve the performance of the evaluation algorithm in a targeted manner here.

Herein, in step S2 it is in principle expedient to select at least the first option, since output data that deviates from the output data supplied by the evaluation algorithm is then always available, i.e. the ground truth does not first have to be ascertained automatically and/or manually. If there are no user changes to the output data for a selected examination process in step S2, a prompt to check and correct the output data can be output to at least one user, in particular the user performing or monitoring the examination process, wherein the output data changed in response thereto is used as training output data.

Then, in a step S3, the additional training data set is ascertained. For this purpose, the input data used in step S1 and the changed output data are assigned to one another, wherein the input data forms the training input data and the user-changed output data forms the training output data.

If the subsequent further training is not to take place on the clinical facility that operates the imaging facility, which will be discussed in more detail below, but on a computing facility of the provider of the evaluation algorithm, which may correspond to the manufacturer of the imaging facility, anonymizing processing of the input data in particular also takes place in step S3. While it is conceivable in a less preferred embodiment for the image data to be reduced to actually required image regions, a preferred embodiment suggests the use of one of the aforementioned first layers of the neural net of the evaluation algorithm that abstractly extracts image characteristics, for example the first layer in order to formulate this abstracted anonymized input data as modified training input data to be fed in after the first layer. In this case, the at least one first layer, by which the input data is anonymized, is not trained. In this case, therefore, it is not the original input data that is used as training input data, but the modified input data resulting from this original input data after processing by at least one first layer of the evaluation algorithm.

Quality-assurance measures can be implemented in an optional step S4. There are also several different possibilities in this regard, wherein it can first be provided that a user confirmation, in particular of the suitability of the changed output data as training output data, is requested. This means the user is, for example informed, that an additional training data set is to be derived from the current examination process and the corresponding information is displayed so that the user can appraise once again whether this suitability exists.

In a second possibility that can be used alternatively or additionally, it is also possible to use concepts that are known in principle that establish a specific distribution of training data sets over case classes, for example a uniform distribution that avoids bias, or also a targeted emphasis of a specific difficult-to-handle case class, which can in particular also be useful when using the second and third option in step S2.

A third particularly preferred option provides that the additional training data set is compared with the basic data training sets already used for training, for which purpose a second similarity measure is determined. If the maximum value of this second similarity measure is below a verification threshold, the ascertained additional training data set appears to deviate highly significantly from the other basic data training sets used so far so that in this case it is provided in step S4 that the potential additional training data set is first stored for checking by a human expert for which purpose it can be marked accordingly.

Before the further training of the evaluation data set takes place in step S6, if, in addition to the training database, the test database used for validation is to be expanded, a suitability condition can be checked, and, when this is fulfilled, it is also possible to take account of previous checks, the potential additional training data set is not used for the further training, but is re-declared as a test data set, and test data for the validation of the evaluation algorithm, i.e. for establishing the outcome of the training, is added. As a result, the additional training data set practically becomes the "test case". In a simple case of a suitability condition, this can simply re-declare every nth additional training data set accordingly; however, further criteria can also be used.

The further training in step S5 now takes place using the additional training data set ascertained in step S3 if this has not been re-declared as a test data set or marked for checking by an expert. Expediently, further training always takes place when a new additional training data set is available. This achieves an improvement of the evaluation algorithm that is as continuous as possible. However, it is also possible, for example, always to accumulate a specific number of additional training data sets, wherein this number is preferably selected to be small, for example less than 10.

The further training in step S5 expediently takes place with the same training method or the same type of machine learning as preceding training measures, in particular the basic training, wherein common known training techniques can be used.

As already mentioned, the training in step S5 can either be performed by the clinical facility using the imaging facility, i.e. on an imaging-facility-side computing facility assigned to the imaging facility or also on the provider-side computing facility, wherein then, as already mentioned, the described anonymization measures have expediently been performed.

Before the now further-trained evaluation algorithm can be provided to imaging facilities, it is validated in a step S6. In the present case, an assessment score is ascertained for the validation in that the further-trained evaluation algorithm is applied to the aforementioned test data. Comparison of the output data ascertained with the test input data by the further-trained evaluation algorithm with the respective test output data enables the performance of the test algorithm, in particular its accuracy, to be checked, wherein the results can be summarized in an assessment score, for example an AUC (area under the curve) value and/or an F1 score. If the improvement of the assessment score exceeds an improvement threshold, the further-trained evaluation algorithm can be provided as an update to the imaging facilities since the improvement is sufficiently significant.

This provision, in particular in the form of a software update, can then take place in a step S7.

It should also be noted at this point that with respect to the reconstruction mentioned with regard to step S1, two approaches can be followed in the method according to the invention. On the one hand, it is conceivable for a clearly defined fixed default reconstruction with default reconstruction parameters to be assumed for the application of the evaluation algorithm, so to speak for the reconstruction to be "standardized" for the evaluation algorithm. In step S1, it is then expedient, in addition to reconstruction with user-desired reconstruction parameters, in each case to additionally perform the default reconstruction with the default reconstruction parameters and to use the resulting image data as input data for the evaluation algorithm, wherein said image data then also becomes part of the additional training data set.

In another approach, it can be provided in step S3, i.e. if the current examination process has been selected to ascertain an additional training data set, that multiple additional data sets are ascertained, since, in addition to the reconstruction performed in step S1 and the image data used there as input data, further reconstructions are performed with different reconstruction parameters in order to determine further conceivable input data to the output data, specifically user-changed output data. This is possible, since the method is used in routine clinical practice and it is still possible to decide during the examination process whether an additional training data set should be ascertained, so that the raw data is usually still available and allows these additional reconstructions. The further training can then take place using all these additional training data sets.

Figure 4:
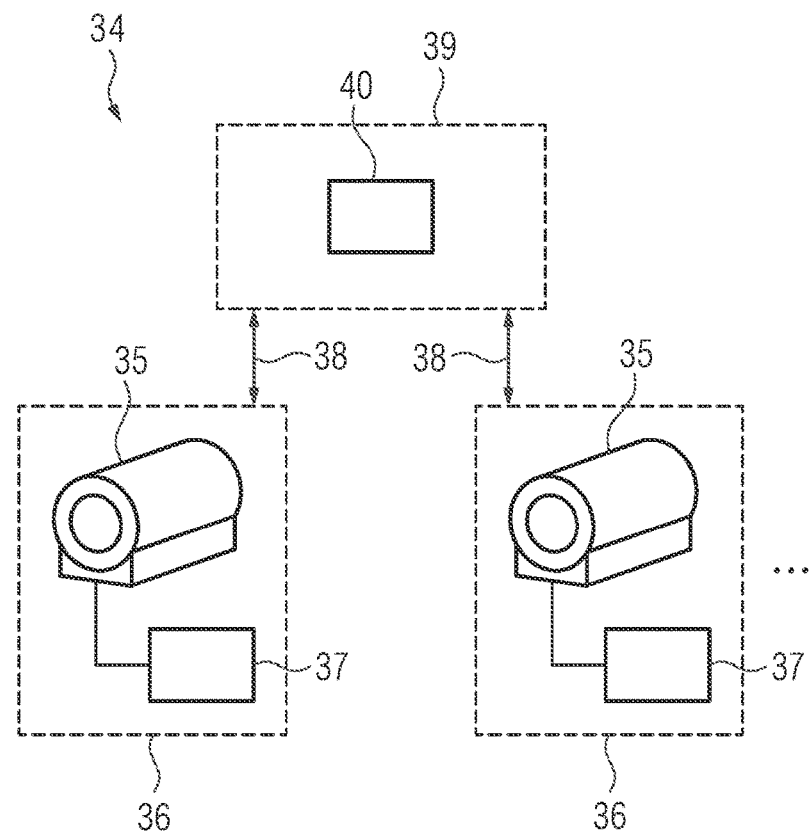
FIG. 4 shows an example embodiment of a training system according to the invention.

FIG. 4 shows a schematic diagram of a training system 34 according to an embodiment of the invention. The training system 34 comprises a plurality of imaging facilities 35 for which the evaluation algorithm is to be used. In the present case, in each case an imaging facility-side computing facility 37 is assigned to these imaging facilities 35 in the region of a clinical facility 36. The imaging facility-side computing facilities 37 communicate via communication links 38 with a provider-side computing facility 40 of a provider 39. As will be explained in more detail, the computing facilities 37, 40 provide functional units for the implementation of the method according to the invention, in particular comprising at least an ascertaining unit and a training unit, wherein corresponding functional variants for different embodiments are explained in more detail in FIGS. 5 and 6.

Figure 5:
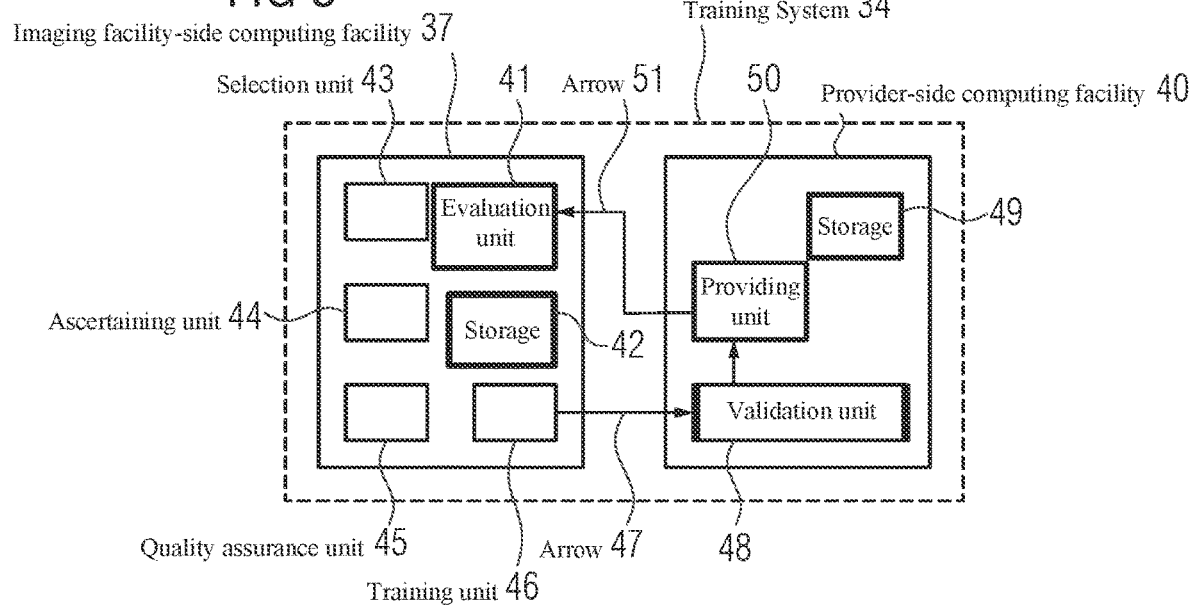
FIG. 5 shows the functional structure of the computing facilities of the training system in a first example embodiment.

According to the embodiment in FIG. 5, the training in step S5 is performed by the imaging-facility-side computing facility 37. In addition to an evaluation unit 41 for the application of the evaluation algorithm (step S1), stored in particular in a storage means 42, the imaging facility-side computing facility 37 initially comprises a selection unit 43, which checks the selection criteria in step S2. An ascertaining unit 44 ascertains the additional training data set according to step S3.

Optionally, the quality assurance measures in step S4 can be implemented in a quality assurance unit 45.

Then, the further training with the additional training data set takes place in the region of the clinical facility 36 in a training unit 46, see step S5, after which the evaluation algorithm further-trained in this way can be transferred to a validation unit 48 of the provider-side computing facility 40 via the communication link 38, see arrow 47. The computing facility 40, which can also have storage means 49, correspondingly also comprises a providing unit 50 via which the further-trained artificial-intelligence evaluation algorithm can be provided again to the evaluation unit 41, see arrow 51. Therefore, the validation unit 48 is embodied to perform step S6 and the providing unit 50 is embodied to perform step S7.

The example embodiment in FIG. 6 differs from the example embodiment in FIG. 5 in that the training unit 46 is provided by the provider-side computing facility 40, i.e. the additional training data set is transferred according to the arrow 52. The ascertaining unit 44 can then accordingly perform the described anonymization measures.

The functional unit shown with regard to FIG. 6 can herein in particular be provided by at least one processor of the computing facilities 37, 40. In particular, in this way, a framework is provided on the interacting computing facilities 37 and 40, which allows at least largely automated further training of the artificial-intelligence evaluation algorithm in a simple and reliable manner.

Although the invention has been illustrated and described in more detail by the preferred example embodiment, the invention is not restricted by the disclosed examples and other variations can be derived herefrom by the person skilled in the art without departing from the scope of protection of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computer-implemented method for further training of a first-trained artificial-intelligence evaluation algorithm that has already been trained based upon basic training data, the first-trained artificial-intelligence evaluation algorithm being trained to ascertain first output data from first input data, the first output data including evaluation results, the first input data including image data recorded during a clinical examination process with a medical imaging facility, and the computer-implemented method comprising:
   ascertaining at least one additional training data set containing training input data and correspondingly assigned training output data in response to determining,
      the training output data has been at least partially correctively modified by a user, and
      the training input data has a first classification based on the training input data being sufficiently similar to at least one first data set, the at least one first data set corresponding to the first classification,
   the training output data being based on an output of the first-trained artificial-intelligence evaluation algorithm ascertained in response to the training input data being input into the first-trained artificial-intelligence evaluation algorithm; and
      further training the first-trained artificial-intelligence evaluation algorithm using the at least one additional training data set to obtain a second-trained artificial-intelligence evaluation algorithm, the training the first-trained artificial-intelligence evaluation algorithm being performed in response to determining that the at least one additional training data set includes a threshold number of additional training data sets.

2. The method of claim 1, further comprising:
   repeating the further training with respect to at least one further additional training data set each time the threshold number of additional training data sets becomes available.

3. The method of claim 1, wherein
   the further training includes performing the further training by an imaging facility-side computing facility assigned to the medical imaging facility; and
   the method further comprises transferring the second-trained artificial-intelligence evaluation algorithm via a communication link to a provider-side computing facility of a provider of the first-trained artificial-intelligence evaluation algorithm.

4. The method of claim 1, further comprising:
   transferring at least one of
      the at least one additional training data set, or
      ascertaining data used to ascertain the at least one additional training data set
   via a communication link to a provider-side computing facility of a provider of the first-trained artificial-intelligence evaluation algorithm,
      wherein the further training includes performing the further training at the provider-side computing facility.

5. The method of claim 4, wherein at least one of:
   the at least one additional training data set, or
   the ascertaining data
   is preprocessed for anonymization prior to being transferred to the provider-side computing facility.

6. The method of claim 5, further comprising:
   restricting a portion of the first-trained artificial-intelligence evaluation algorithm to be further trained as unchangeable by defining at least one first layer of the first-trained artificial-intelligence evaluation algorithm, wherein
      the ascertaining the at least one additional training data set includes ascertaining original input data already processed by the at least one first layer of the first-trained artificial-intelligence evaluation algorithm as the training input data, and
the method further comprises transmitting the training input data to the provider-side computing facility.

7. The method of claim 3, further comprising:
providing the second-trained artificial-intelligence evaluation algorithm only after assessing, on the provider-side computing facility, the second-trained artificial-intelligence evaluation algorithm for application on at least the medical imaging facility; and
ascertaining an assessment score, by the provider-side computing facility, for the assessing.

8. The method of claim 1, further comprising:
selecting an examination process for the ascertaining the at least one additional training data set, the examination process being based on at least one of:
respective output data of the first-trained artificial-intelligence evaluation algorithm having been changed by a respective user,
the first-trained artificial-intelligence evaluation algorithm outputting an uncertainty measure that exceeds an uncertainty threshold, the uncertainty measure corresponding to an uncertainty corresponding to the respective output data, or
a first similarity measure is ascertained that exceeds a selection threshold, the first similarity measure being ascertained between at least respective input data and the at least one first data set, the first classification corresponding to a high degree of uncertainty or a failure rate for the first-trained artificial-intelligence.

9. The method of claim 8, wherein
the selected examination process is based on the respective output data of the first-trained artificial-intelligence evaluation algorithm having been changed by the respective user; and
the method further comprises outputting a prompt to the respective user to check and correct the respective output data in response to the respective user not having changed the respective output data for a selected examination process, the respective output data changed in response to the prompt being used as respective training output data.

10. The method of claim 1, further comprising:
ascertaining at least one second similarity measure after the ascertaining the at least one additional training data set, the at least one second similarity measure being ascertained with training data sets of the basic training data;
marking the at least one additional training data set for checking by a human expert upon a maximum similarity measure among the at least one second similarity measure falling below a verification threshold; and
storing the at least one additional training data for the checking by the human expert.

11. The method of claim 1, further comprising:
reconstructing raw data obtained with the medical imaging facility to form the image data using at least one default reconstruction parameter, the reconstruction being performed by the medical imaging facility independently of a user reconstruction, and the image data ascertained using the at least one default reconstruction parameter being the training input data.

12. The method of claim 1, further comprising:
performing a user-requested reconstruction of raw data obtained with the medical imaging facility to form the image data used as the training input data, and at least one further default reconstruction of the raw data to form further image data, the further image data being used as further training input data for further additional training data sets using the training output data.

13. A training system, comprising:
at least one medical imaging facility including an imaging facility-side computing facility assigned to the at least one medical imaging facility, the imaging facility-side computing facility being configured to execute a first-trained artificial-intelligence evaluation algorithm that has already been trained based upon basic training data, the first-trained artificial-intelligence evaluation algorithm being trained to ascertain first output data from first input data, the first output data including evaluation results, the first input data including image data recorded during a clinical examination process with the at least one medical imaging facility; and
a provider-side computing facility of a provider of the first-trained artificial-intelligence evaluation algorithm, the provider-side computing facility being connected to the imaging facility-side computing facility via a communication link, at least one of the provider-side computing facility or the imaging facility-side computing facility being configured to:
ascertain at least one additional training data set containing training input data and correspondingly assigned training output data in response to determining,
the training output data has been at least partially correctively modified by a user, and
the training input data has a first classification based on the training input data being sufficiently similar to at least one first data set, the at least one first data set corresponding to the first classification,
the training output data being based on an output of the first-trained artificial-intelligence evaluation algorithm ascertained in response to the training input data being input into the first-trained artificial-intelligence evaluation algorithm, and
train the first-trained artificial-intelligence evaluation algorithm using the at least one additional training data set to obtain a second-trained artificial-intelligence evaluation algorithm, the first-trained artificial-intelligence evaluation algorithm being trained in response to determining that the at least one additional training data set includes a threshold number of additional training data sets.

14. A non-transitory computer-readable medium storing a computer program that, when executed on a training system, causes the training system to perform the method of claim 1.

15. The method of claim 2, wherein
the further training includes performing the further training by an imaging facility-side computing facility assigned to the medical imaging facility; and
the method further comprises transferring the second-trained artificial-intelligence evaluation algorithm via a communication link to a provider-side computing facility of a provider of the first-trained artificial-intelligence evaluation algorithm.

16. The method of claim 2, further comprising:
transferring at least one of
the at least one additional training data set, or
ascertaining data used to ascertain the at least one additional training data set
via a communication link to a provider-side computing facility of the provider of the first-trained artificial-intelligence evaluation algorithm, wherein the further includes performing the further training at the provider-side computing facility.

17. The method of claim 16, wherein at least one of:
the at least one additional training data set, or
the ascertaining data
is preprocessed for anonymization prior to being transferred to the provider-side computing facility.

18. The method of claim 17, further comprising:
restricting a portion of the first-trained artificial-intelligence evaluation algorithm to be further trained as unchangeable by defining at least one first layer of the first-trained artificial-intelligence evaluation algorithm, wherein
the ascertaining the at least one additional training data set includes ascertaining original input data already processed by the at least one first layer of the first-trained artificial-intelligence evaluation algorithm as the training input data, and
the method further comprises transmitting the training input data to the provider-side computing facility.

19. The method of claim 15, further comprising:
providing the second-trained artificial-intelligence evaluation algorithm only after assessing, on the provider-side computing facility, the second-trained artificial-intelligence evaluation algorithm for application on at least the medical imaging facility; and
ascertaining an assessment score, by the provider-side computing facility, for the assessing.

20. The method of claim 2, further comprising:
selecting an examination process for the ascertaining the at least one additional training data set, the examination process being based on at least one of:
respective output data of the first-trained artificial-intelligence evaluation algorithm having been changed by a respective user,
the first-trained artificial-intelligence evaluation algorithm outputting an uncertainty measure that exceeds an uncertainty threshold, the uncertainty measure corresponding to an uncertainty corresponding to the respective output data, or
a first similarity measure is ascertained that exceeds a selection threshold, the first similarity measure being ascertained between at least respective input data and the at least one first data set, the first classification corresponding to a high degree of uncertainty or a failure rate for the first-trained artificial-intelligence.

21. The method of claim 1, wherein all of the image data has been reconstructed using the same standardized reconstruction parameter, the training input data including the image data.

22. The method of claim 1, wherein the evaluation results include control parameters for controlling the medical imaging facility.

23. The method of claim 1, wherein
the first-trained artificial-intelligence evaluation algorithm is trained to ascertain an uncertainty measure and the first output data from the first input data; and
the ascertaining ascertains the at least one additional training data set in response to determining:
the training output data has been at least partially correctively modified by a user,
the uncertainty measure corresponding to the training output data exceeds an uncertainty threshold, and
the training input data has a first classification based on a similarity between the training input data and at least one first data set, the at least one first data set corresponding to the first classification.

* * * * *